United States Patent [19]

Sheads et al.

[11] 4,436,665

[45] Mar. 13, 1984

[54] TWO SOLVENT PROCESS FOR PREPARATION OF ESTERS OF 3,5-DIBROMO-4-HYDROXYBENZONITRILE

[75] Inventors: Richard E. Sheads, Durham, N.C.; David A. Segal, Hatfield, Pa.

[73] Assignee: Union Carbide Corporation, Danbury, Conn.

[21] Appl. No.: 426,733

[22] Filed: Sep. 29, 1982

[51] Int. Cl.$^3$ .......................................... C07C 121/75
[52] U.S. Cl. .............................. 260/404; 260/465 D; 260/465 F
[58] Field of Search ................ 260/465 D, 465 F, 404

[56] References Cited

U.S. PATENT DOCUMENTS

| | | | |
|---|---|---|---|
| 3,349,111 | 10/1967 | Luckenbaugh | 260/465 F |
| 3,397,054 | 8/1968 | Hart et al. | 71/105 |
| 3,592,626 | 7/1971 | Heywood et al. | 71/70 |
| 3,671,556 | 6/1972 | Goldstick | 260/404 |
| 4,332,613 | 6/1982 | Esposito | 71/105 |
| 4,349,488 | 9/1982 | Dentel et al. | 260/465 D |

OTHER PUBLICATIONS

Product Review, "Bromine Chloride: An Alternative to Bromine", Jack F. Mills and John A. Schneider, The Dow Chemical Company, Midland, Mich., 48640.
Britton et al., Chemical Abstracts, vol. 47, p. 5437, (1953).

Primary Examiner—Dolph H. Torrence
Attorney, Agent, or Firm—J. A. Shedden

[57] ABSTRACT

Esters of 3,5-dibromo-4-hydroxybenzonitrile can be prepared in high yields from 4-cyanophenol by reacting said phenol with preformed bromine chloride in 3% aqueous hydrogen bromide and then azeotropically distilling off the solvent/reaction medium with an aromatic hydrocarbon which then serves as the esterifying solvent medium for reaction with an acid halide. In this manner, both reactions can be accomplished without removing the product of the bromination reaction from the reaction vessel, i.e., a solids separation step is avoided.

13 Claims, No Drawings

TWO SOLVENT PROCESS FOR PREPARATION OF ESTERS OF 3,5-DIBROMO-4-HYDROXYBENZONITRILE

FIELD OF THE INVENTION

This invention relates to a novel method of preparing esters of 3,5-dibromo-4-hydroxybenzonitrile.

BACKGROUND OF THE INVENTION

Certain esters of the 3,5-dichloro; 3,5-dibromo-; and 3,5-diiodo-4-hydroxybenzonitriles, also known respectively as chloroxynil, bromoxynil and ioxynil are extensively used as broadleaf weed herbicides, particularly in crop-growing areas.

Examples of such esters are those formed from the 3,5-dichloro-, 3,5-dibromo-, or 3,5-diiodo-4-hydroxybenzonitriles and unsubstituted or halogenated aliphatic, cycloaliphatic or aromatic acids, such as trichloroacetic, propionic, 2,2-dichloropropionic, n-butanoic, n-octanoic, 2-ethylhexanoic, cyclohexylcarboxylic, benzoic and benzenesulfonic acids.

Three synthesis of these herbicides from the dihalohydroxybenzonitriles have been described in the prior art.

U.S. Pat. No. 3,592,626 (Heywood et al) details two methods. According to one, the 3,5-dihalo-4-hydroxybenzonitrile is reacted with an organic anhydride in the presence of a condensing agent, such as concentrated sulfuric acid or a sodium or potassium salt of the corresponding organic acid. According to the other method, the benzonitrile derivative is reacted with an acid halide, e.g., the chloride, in the presence of a tertiary base, e.g., pyridine, or in the presence of a quaternary ammonium salt, e.g. tetralkylammonium chloride.

Both of these methods have disadvantages and shortcommings.

In the anhydride method, only one-half of the acid equivalent of the anhydride is reacted with the hydroxybenzonitrile, the other half is converted into free acid which must be removed from the reaction mixture and is essentially a waste product. Also, the removal of the condensing agent, sulfuric acid or alkali salt of the organic acid, needs additional processing and causes extra expenses when the ester of the benzonitrile is needed in a purified form.

The use of tertiary bases, such as pyridine, usually in excess, in the second method mentioned is expensive and complicates the synthesis process for the following reason. Most of the base has to be recovered for reuse, necessitating an appropriate separation step such as distillation. The portion of the base which served as acceptor for the hydrogen chloride formed requires other processing steps as it has to be separated from the ester product.

The variant of the acid chloride method carried out in the presence of quaternary salts has the disadvantage of employing these rather costly salts. Their direct recovery for reuse is expensive, if not impossible and even the separation of these salts from the product ester involves such steps as addition of solvent, neutralization and crystallization.

U.S. Pat. No. 3,671,556 (Goldstick) discloses a third method for the preparation of esters of 3,5-dihalo-4-hydroxybenzonitriles. It is taught that the esters can be formed by the direct reaction of the hydroxybenzonitrile derivatives with the appropriate acid halides, if the dry, solid hydroxybenzonitrile is gradually added to a slight excess of the liquid acid halide, e.g. capryloyl chloride, kept at a temperature above 120° C. The reaction need not be carried out in the presence of any base, acid acceptor, catalyst or condensing agent, however, it is suggested that in the case where the acid chloride is unusually viscous or high-melting, a solvent can be used.

All of the above processes, of course, anticipate preparing the esters from a previously isolated dihalohydroxybenzonitrile reactant.

With regard to the preparation of these dihalohydroxybenzonitrile reactants, E. Muller et al, Chem. Ber. 92, 2278(1959) teaches that p-hydroxybenzonitrile should be dissolved in methanol and glacial acetic acid and then treated with bromine. The product is then poured into an aqueous methanolic solution of $NaHSO_3$.

Luckenbaugh (U.S. Pat. No. 3,349,111) discloses that 3,5-dibromo-4-hydroxybenzonitrile can be prepared by reacting an aqueous suspension of p-hydroxybenzonitrile with aqueous alkali metal hydroxide or aqueous alkali metal carbonate; reacting the mixture with bromine; further reacting this mixture with chlorine; then acidifying the mixture and finally filtering to obtain the product. An alternative process eliminates the base.

All of the prior art processes require that the dihalohydroxybenzonitrile intermediate be isolated usually by filtration, from the bromination reaction medium before esterification can be realized because the prior art bromination solvent/reaction media are incompatable with the prior art esterification/solvent media. This necessitates, at least at some stage, removal of the intermediate dihalohydroxybenzonitrile from the bromination reactor before the esterification process.

SUMMARY OF THE INVENTION

In accordance with the present invention, it has been discovered that esters of 3,5-dibromo-4-hydroxybenzonitrile can be prepared in high yields from 4-cyanophenol without isolation of the 3,5-dibromo-4-hydroxybenzonitrile intermediate, i.e., both the bromination and esterification reactions can be accomplished without removing the product of the bromination reaction from the reaction vessel.

4-cyanophenol can be dibrominated with (1) bromine; (2) bromine and chlorine either sequentially or at the same time; or preferably (3) preformed bromine chloride in water or most preferably 3% aqueous hydrogen bromide. The water, hydrochloric acid and hydrobromic acid are azeotropically removed by an aromatic hydrocarbon which then serves as the esterification solvent medium. In this manner, esters of 3,5-dibromo-4-hydroxybenzonitrile are prepared from 4-cyanophenol without the necessity of a solids separation step.

The overall reaction can be illustrated by the following:

Step 1 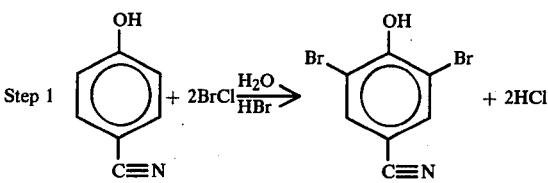

Step 2 SOLVENT EXCHANGE:

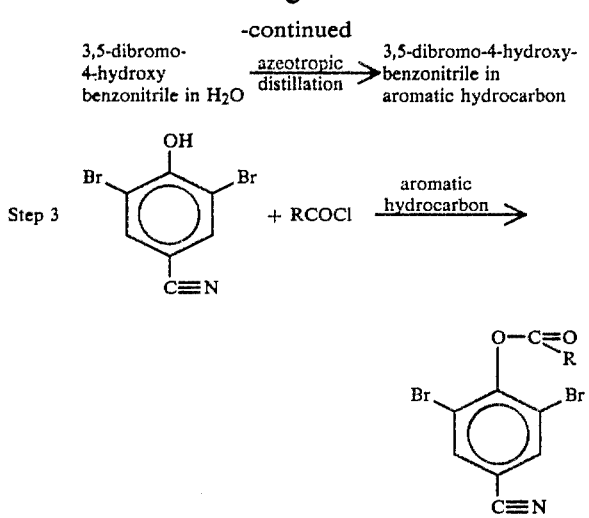

The organic groups designated by the symbol R are intended to include all of the usual organic acid moieties i.e., aliphatic, cycloaliphatic, or aromatic which are available as the corresponding acid chloride.

DETAILED DESCRIPTION OF THE INVENTION

The invention relates to the discovery that 4-cyanophenol can be brominated using preformed bromine chloride in a 3% aqueous hydrogen bromide solvent; the water, hydrochloric acid and hydrobromic acid medium azeotropically removed via an aromatic hydrocarbon; and the 3,5-dibromo-4-hydroxybenzonitrile intermediate esterified in said aromatic hydrocarbon: all of the above realizable without a solids separation step.

A detailed discussion regarding the properties of preformed bromine chloride can be found in "Bromine Chloride: An Alternative to Bromine", *Ind. Eng. Chem. Prod. Res. Develop.* Vol 12 3 1973 by Mills and Schneider.

The preferred acid halides are the chlorides, particularly the aliphatic acids, both straight and branched chain, having from 3 to 18 carbon atoms and most preferably from 4 to 12 carbon atoms. Substituted aliphatic acid groups wherein one or more of the hydrogen atoms has been replaced by a functional group such as halo are also included. Suitable aromatic acids are the aralkanoic acids such as benzoic acid and the same where the aromatic moiety is substituted with functional groups such as $C_1$ to $C_5$ alkyl, halo, sulfonyl, trifluoromethyl, nitro and the like.

The preferred acid chlorides used in the process of this invention are those having a boiling point above about 100° C. though lower boiling acid chlorides can be used in which case the reaction is suitably carried out at an elevated pressure sufficient to attain a reaction temperature of about 100° C. or higher while maintaining the acid chloride in the liquid phase.

The aromatic hydrocarbons contemplated for use in this invention are those which form an azeotrope with water at from about 100° C. to about 150° C. and provide a solvent medium for the 3,5-dibromo-4-hydroxybenzonitrile intermediate under refluxing conditions. The preferred aromatic hydrocarbons are the xylenes, toluene and benzene. The bromination reaction is conducted at from about 75° C. to about 100° C. with the lower temperatures being preferred to reduce hydrolysis of the 3,5-dibromo-4-hydroxybenzonitrile to 3,5-dibromo-4-hydroxybenzamide and 3,5-dibromo-4-hydroxybenzoic acid.

The esterification reaction mixture is refluxed until the reaction is completed usually at temperatures in excess of 100° C.; more usually in excess of 110° C.

It has been discovered that the use of 3% aqueous hydrogen bromide during the bromination reaction with bromine chloride, suppresses the competitive chlorination reactions which can result in by-product formation of, e.g., 2-bromo-6-chloro-4-cyanophenol and 4-cyano-2,6-dichlorophenol. With the process of this invention, chlorinated by-product formation can be lowered to less than 1%.

In general, after the bromination is complete, excess bromine chloride is distilled off and aromatic hydrocarbon is added to remove by azeotropic distillation the water and both of the mineral acids, i.e., hydrochloric and hydrobromic acid.

As both the distillation temperature and the percent of the mineral acids increase, the possibility of hydrolyzing bromoxynil phenol to the benzamide and benzoic acid derivatives increases. The degree of this hydrolysis can be reduced by rapid azeotropic distillation of the aqueous phase.

Once the system is anhydrous, the acid halide is added and the reaction heated to complete the esterification. Usually an excess of the acid halide is used, e.g., from about 5 to about 10%, to assist in driving the reaction to completion.

The reaction can be quenched with methanol which converts any unreacted acid halide. The aromatic hydrocarbon solvent along with most of the converted acid halide is distilled off, leaving as a molten residue the desired ester.

Atmospheric pressure is usually employed in effecting the reactions according to the process of the instant invention. However, pressures both above and below atmospheric pressure can also be employed whenever it is desirable to do so.

The following example is set forth for purposes of illustration so that those skilled in the art may better understand the invention, and it should be understood that it is not to be construed as limiting this invention in any manner.

EXAMPLE 1

Synthesis of octanoate ester of 3,5-dibromo-4-hydroxybenzonitrile

To 66 g. (0.554 mole) of 4-cyanophenol slurried in 385 ml of 3% aqueous hydrobromic acid in a 1 liter resin flask equipped with a three-paddle stirring shaft and air-powered and heated to 80° C. was added bromine chloride directly from the cylinder over four hours. After the bromination is complete, the excess bromine chloride is removed by distillation. The water distilling off becomes colorless when the excess bromine chlorine is removed. A total of 385 ml of xylene is added and the azeotrope of xylene with water, hydrochloric acid, and hydrobromic acid is distilled off. To the anhydrous xylene at 100° C. is added 100 ml of octanoyl chloride (7% excess) over a period of one hour. The reaction is then heated to reflux for five hours. The reaction is cooled to 60° C. and 10 ml of methanol added to removed excess acid chloride. The solvent is distilled off and three fractions are collected: (1) a low boiling fraction containing methanol and xylene (2%); (2) a middle fraction consisting of xylene (80%); and (3) a high boiling fraction (18%) consisting of xylene and methyl octanoate obtained by applying a vacuum of 50 mm and heating to 150°. A total of 220 g of final product is obtained as residue in the pot, mp 35°–40° C. The gc (Internal Standard) showed a purity of 87.6% and gave a yield of 86%.

We claim:

1. A method of preparing esters of 3,5-dibromo-4-hydroxybenzonitrile from 4-cyanophenol which comprises:
    (a) reacting said 4-cyanophenol with a reactant(s) selected from the group consisting of bromine; bromine and chlorine; and preformed bromine chloride in water or 3% aqueous hydrogen bromide;
    (b) azeotropically distilling the resulting solvent medium with an aromatic hydrocarbon; and
    (c) reacting the 3,5-dibromo-4-hydroxybenzonitrile intermediate in said aromatic hydrocarbon with an acid halide selected from the group consisting of an aliphatic, cycloaliphatic and aromatic acid halide.

2. A method of preparing esters of 3,5-dibromo-4-hydroxybenzonitrile from 4-cyanophenol which comprises:
    (a) reacting said 4-cyanophenol with a reactant(s) selected from the group consisting of bromine; bromine and chlorine; and preformed bromine chloride in 3% aqueous hydrogen bromide;
    (b) azeotropically distilling the resulting solvent medium with an aromatic hydrocarbon; and
    (c) reacting the 3,5-dibromo-4-hydroxybenzonitrile intermediate in said aromatic hydrocarbon with an acid halide selected from the group consisting of an aliphatic, cycloaliphatic and aromatic acid halide.

3. A method of preparing esters of 3,5-dibromo-4-hydroxybenzonitrile from 4-cyanophenol which comprises:
    (a) reacting said 4-cyanophenol with preformed bromine chloride in 3% aqueous hydrogen bromide;
    (b) azeotropically distilling the resulting solvent medium with an aromatic hydrocarbon; and
    (c) reacting the 3,5-dibromo-4-hydroxybenzonitrile intermediate in said aromatic hydrocarbon with an acid halide selected from the group consisting of an aliphatic, cycloaliphatic and aromatic acid halide.

4. A method of preparing esters of 3,5-dibromo-4-hydroxybenzonitrile from 4-cyanophenol which comprises:
    (a) reacting said 4-cyanophenol with preformed bromine chloride in 3% aqueous hydrogen bromide;
    (b) azeotropically distilling the resulting solvent medium with an aromatic hydrocarbon; and
    (c) reacting the 3,5-dibromo-4-hydroxybenzonitrile intermediate in said aromatic hydrocarbon with an aliphatic acid halide.

5. The method of claim 4 wherein said aliphatic acid halide is a chloride of straight or branched alkanoic acids having from 3 to 18 carbon atoms.

6. The method of claim 5 wherein said straight or branched alkanoic chloride has from 4 to 12 carbon atoms.

7. The method of claim 6 wherein said alkanoic chloride is octanoyl chloride.

8. The method of claim 6 wherein said alkanoic chloride is butyryl chloride.

9. The method of claim 4 wherein one or more of the hydrogen atoms on said aliphatic acid halide have been replaced by a halogen.

10. A method of preparing esters of 3,5-dibromo-4-hydroxybenzonitrile from 4-cyanophenol which comprises:
    (a) reacting said 4-cyanophenol with preformed bromine chloride in 3% aqueous hydrogen bromide;
    (b) azeotropically distilling the resulting solvent medium with an aromatic hydrocarbon; and
    (c) reacting the 3,5-dibromo-4-hydroxybenzonitrile intermediate in said aromatic hydrocarbon with an aromatic acid halide.

11. The method of claim 10 wherein said aromatic acid halide is selected from the group consisting of unsubstituted benzoic acid halide and substituted benzoic acid halide wherein the substituents are selected form the group consisting of $C_1$ to $C_5$ alkyl, halo, sulfonyl, trifluoromethyl, and nitro.

12. A method of preparing esters of 3,5-dibromo-4-hydroxybenzonitrile from 4-cyanophenol which comprises:
    (a) reacting said 4-cyanophenol with preformed bromine chloride in 3% aqueous hydrogen bromide;
    (b) azeotropically distilling the resulting solvent medium with an aromatic hydrocarbon selected from the group consisting of the xylenes, toluene and benzene; and
    (c) reacting the 3,5-dibromo-4-hydroxybenzonitrile intermediate in said aromatic hydrocarbon with an acid halide selected from the group consisting of an aliphatic, cycloaliphatic and aromatic acid halide.

13. The method of claim 12 wherein said aromatic hydrocarbon is selected from the group consisting of the xylenes.

* * * * *